United States Patent
Van der AA et al.

[11] Patent Number: 5,858,006
[45] Date of Patent: Jan. 12, 1999

[54] HYPODERMIC NEEDLE WITH A PROTRUSION

[75] Inventors: Bartholomeus W. J. Van der AA, Delft; Franciscus H. C. Benning, Almelo, both of Netherlands

[73] Assignee: Texas Instruments Incorporated, Dallas, Tex.

[21] Appl. No.: 142,276

[22] Filed: Oct. 26, 1993

[51] Int. Cl.$^6$ .............................. A61M 5/00; A61M 5/32
[52] U.S. Cl. ............................... 604/239; 604/272
[58] Field of Search .................... 604/272–274, 604/239, 22, 117, 130, 134, 135, 240, 243; 128/763, 770, 751, 749, 753, 754; 606/167, 170, 171

[56] References Cited

U.S. PATENT DOCUMENTS

| | | | |
|---|---|---|---|
| 1,274,081 | 7/1918 | Riethmueller | 604/117 |
| 3,209,695 | 10/1965 | Crockford et al. | 604/130 |
| 3,277,893 | 10/1966 | Clark . | |
| 4,735,611 | 4/1988 | Anderson et al. | 604/130 |
| 4,795,446 | 1/1989 | Fecht | 604/264 |
| 4,863,428 | 9/1989 | Chevalier | 604/130 |
| 5,364,373 | 11/1994 | Wasköng et al. | 604/272 |

FOREIGN PATENT DOCUMENTS

| | | |
|---|---|---|
| A-2 057 353 | 5/1971 | France . |
| C-346 472 | of 0000 | Germany . |

*Primary Examiner*—John D. Yasko
*Assistant Examiner*—Sharon Finkel
*Attorney, Agent, or Firm*—Rebecca Mapstone-Lake; David Denker; Richard L. Donaldson

[57] ABSTRACT

Hypodermic needle 2 is to be introduced between the skin and the tissue adjacent to the skin. To separate the skin from the tissue, cartilage or bone below the skin and to prevent the tip 6 of the needle 2 from piercing the tissue below the skin this invention discloses providing the extremity 6 of the needle with a protrusion 4. To prevent damage to the living being in which the needle 2 is introduced the transition of the protrusion 4 to the needle is smooth in all directions. The protrusion 4 is provided on that side of the needle which will be adjacent to the tissue, cartilage or bone of the living being.

5 Claims, 1 Drawing Sheet

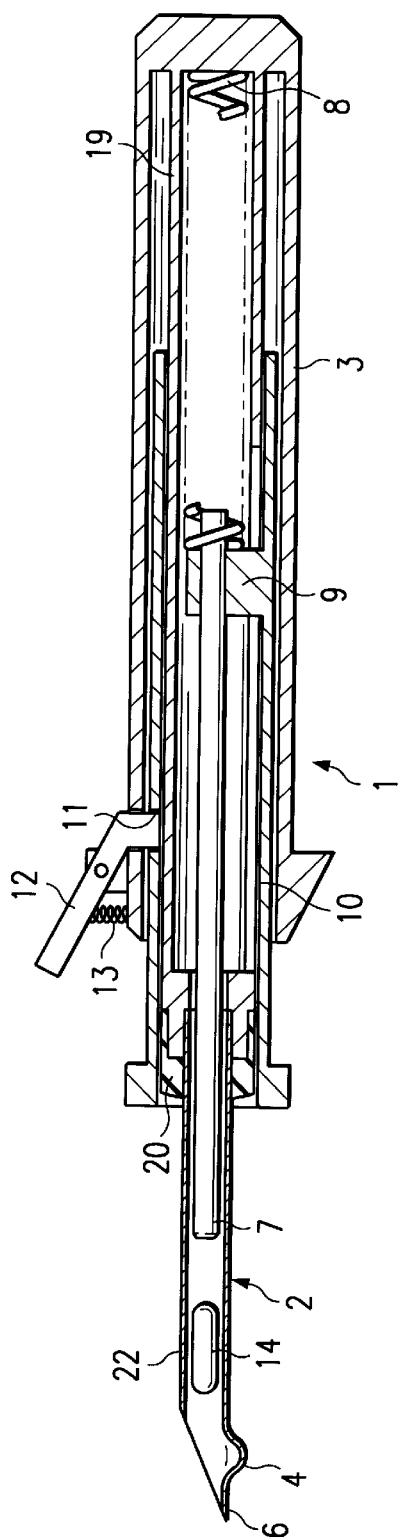
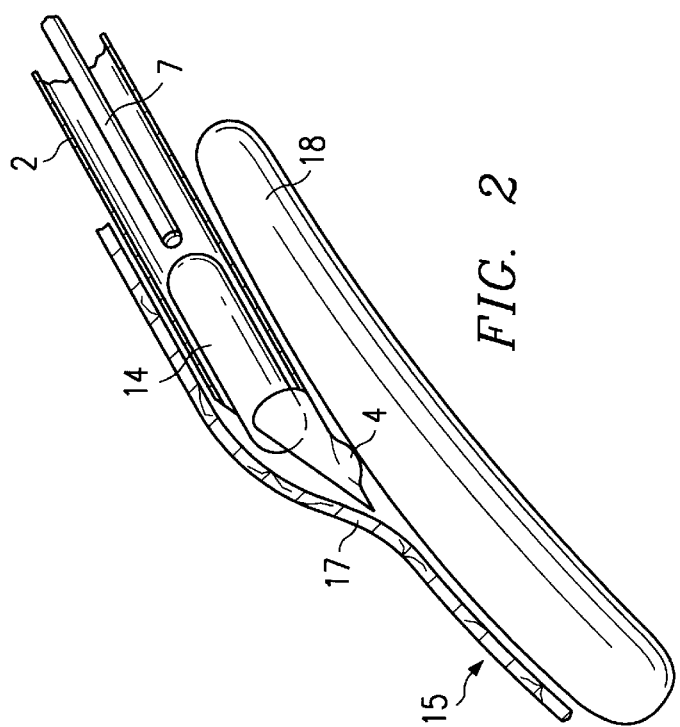

HYPODERMIC NEEDLE WITH A PROTRUSION

BACKGROUND OF THE INVENTION

The invention relates to apparatus for injection of solid non-deformable articles into living creatures and more specifically to the needles used in such apparatus.

In related apparatus shown in U.S. Pat. No. 3,277,893, the protrusion described functions as a barb. The needle disclosed therein is designed to be shot in animals from a considerable distance. In that case it is important that the needle will remain in the skin of the animal. Normally such a needle is shot perpendicular to the surface of such an animal.

In the art, hypodermic needles are used to insert solids and fluids, such as transponders, or drugs immediately below the skin and parallel to the skin. To that end, an opening is pierced through the skin of the living being by the needle. After that, the needle is often tilted such that it is moved parallel to the skin. During this movement it is important that the skin is lifted from the underlying tissue, bone or cartilage. Furthermore, it is important that the tip of the needle will not pierce in the tissue below the skin. This means that the operator must be able to find his way below the skin of the living being with the needle without being able to see the tip of the needle.

SUMMARY OF THE INVENTION

One purpose of the invention is to realize a needle which makes it possible to clearly define the path between the lower side of the skin and the upper side of the tissue, cartilage or bone below the skin.

According to the invention, the protrusion is used to guide the lower side of the needle over the tissue, cartilage or bone of the living being. Because of its smooth character, this tissue below the skin will not be attacked and the tip of the needle will be kept a selected distance above such a tissue. Of course, it is possible to easily remove such a needle. This is in contrast with the barbed needle according to U.S. Pat. No. 3,277,893. The position of introduction of the needle according to the specification of U.S. Pat. No. '893 is of no importance because it will generally be introduced perpendicularly to the surface of the animal. This is in contrast with the needle according to the present invention.

A substantially smooth transition face between the protrusion and the needle of this invention is obtained since the transition between the various parts of the protrusion is circular. Of course, the needle is hollow to allow introduction of objects or drugs the needle is hollow.

According to a further preferred embodiment of the invention, the tip of the needle is bevelled and the farthest extremity positioned to be placed remote from the skin of the living being after the introduction of the needle under the skin. The tip of the needle is first used to pierce the skin and after that the needle is tilted and the protrusion at the tip functions to lift the skin from the underlying tissue, cartilage or bone.

Although, the protrusion can be realized on the outside surface of most needles, according to a preferred embodiment of this invention, the tip of the needle is provided with a depression to realize the protrusion. It is also possible to connect a protrusion-shaped part (which may be made of any suitable material including plastic) to the circumference of the needle.

BRIEF DESCRIPTION OF THE DRAWINGS

The invention will be further explained referring to a preferred embodiment of the invention shown in the drawing, wherein:

FIG. 1 shows in cross section an apparatus provided with the needle according to the invention; and FIG. 2 shows the tip of the needle during insertion in a living being.

DESCRIPTION OF THE INVENTION

In FIG. 1, an injector 1 is shown comprising a housing 3 and needle 2. The needle 2 is rigidly connected to sleeve 19 at the base portion 20 which in turn is connected to housing 3 through sleeve 19. In addition to the base portion 20, needle 2 includes a hollow cylindrical shaft portion defined by a sidewall 22, and is provided near its extremity 6 with a protrusion 4. This protrusion 4 may be provided by depressing a part of the wall of needle 6 as shown, or could be a separate member attached to the needle. Regardless of how the protrusion 4 is formed, it is important that the transition from the protrusion to the shaft be smooth in all directions. The outer part of housing 3 is provided with a trigger 12 which can be actuated against a spring 13. Trigger 12 is designed to engage an opening 11 in sleeve 10. Sleeve 10 is provided with a support block 9 in which a pushing rod 7 is mounted. One side of pushing rod 7 is introduced in hollow needle 2 whilst a protruding end of it acts to receive a compression spring 8 which on the other hand engages on housing 3. Reference number 14 indicates a product to be introduced in an animal such as a drug or a transponder used for identifying animals.

The apparatus shown in FIG. 1 functions as follows.

In the position shown in FIG. 1, spring 8 is under compression. In this condition, the needle is introduced under the skin of the animal as will be further explained with regard to FIG. 2. After complete introduction of the needle and still in the position of FIG. 1, trigger 12 is actuated. Because of force of spring 8, action on support block 9, and releasing of sleeve 10 through trigger 12, sleeve 10 moves outwardly relative to housing 3. During this movement pushing rod 7 will also move outwardly. However, in practice this means that pushing rod 7 will remain stationary whilst needle 2 and housing 3 will retract from the animal. In the end position, not shown, the needle will be completely received in sleeve 10 so that there is no danger from the tip 6 of the needle. During this retracting movement, product 14 will remain in position under the skin of the animal and will be placed after removing apparatus 1 from the animal.

In FIG. 2 the introduction of the injector 1 according to the invention is shown. After introduction of the needle in the skin 17 according to any method known in the art the needle has to be positioned between skin 17 and cartilage 18 being immediately under the skin. Such a structure is, e.g., found in ears of most animals. It is important that the needle is displaced over a considerable distance between skin 17 and cartilage 18 to be able to position transponder 14 on a desired location. To prevent the tip 6 of the needle attacking cartilage 18 ball-shaped protrusion 4 is provided which guides the extremity 6 of the needle over the surface of cartilage 18. Through this movement skin 17 of part 15 of the living being is separated from cartilage 18.

Although the invention is described above with reference to a simple embodiment of an apparatus provided with the needle according to the invention it has to be understood that further guiding members can be provided to guarantee that the path of the needle between the skin and the tissue below is a predetermined path.

What is claimed:

1. A hypodermic needle having at least a base portion, a hollow shaft portion and a tip or extremity portion all formed of the same material for use with apparatus for injecting a substantially non-deformable article into the tissue of a live animal comprising:

the base portion for attaching said hypodermic needle to injection apparatus;

the hollow shaft portion extending between said base portion and a tip portion, said shaft portion defined by a sidewall, said hollow shaft defining a passage through said needle for the substantially non-deformable article;

the tip or extremity portion of said needle for piercing the skin and tissue of the live animal; and a protrusion formed on said sidewall of said needle proximate said extremity portion, said protrusion being formed as a part of said hollow shaft portion such that the transition from the protrusion to the shaft of said needle is smooth in all directions including the portion of the protrusion closest to said base portion such that said protrusion will not act as a barb and said needle will be easy to remove, said protrusion being positioned on the needle so as to be near said tip or extremity portion so as to protect tissue such as cartilage or bone of said live animal.

2. The hypodermic needle according to claim 1, and further including apparatus attached for injecting a substantially non-deformable article, said apparatus for injecting including a needle pusher means for moving in the passage of said needle to move said substantially non-deformable article through the needle and into the tissue of said animal.

3. The hypodermic needle according to claim 1, wherein the transition between various parts of said protrusion is circular.

4. The hypodermic needle according to claim 1, wherein the tip of the needle is bevelled.

5. The hypodermic needle according to claim 1, wherein said protrusion comprises a depressed part of the needle sidewall.

* * * * *